United States Patent
Patrickson et al.

(10) Patent No.: US 10,438,497 B2
(45) Date of Patent: Oct. 8, 2019

(54) SYSTEM AND METHOD FOR MAINTENANCE OF COMPETENCE

(71) Applicant: LAERDAL MEDICAL AS, Stavanger (NO)

(72) Inventors: Clive William Patrickson, Goshen, NY (US); Kenneth George Morallee, Orpington (GB)

(73) Assignee: Laerdal Medical AS, Stavanger (NO)

( * ) Notice: Subject to any disclaimer, the term of this patent is extended or adjusted under 35 U.S.C. 154(b) by 231 days.

(21) Appl. No.: 14/379,297

(22) PCT Filed: Feb. 4, 2013

(86) PCT No.: PCT/EP2013/052138
§ 371 (c)(1),
(2) Date: Aug. 17, 2014

(87) PCT Pub. No.: WO2013/120720
PCT Pub. Date: Aug. 22, 2013

(65) Prior Publication Data
US 2015/0010892 A1    Jan. 8, 2015

Related U.S. Application Data

(60) Provisional application No. 61/600,101, filed on Feb. 17, 2012.

(51) Int. Cl.
*G09B 5/00* (2006.01)
*G09B 9/00* (2006.01)
(Continued)

(52) U.S. Cl.
CPC ............ *G09B 5/00* (2013.01); *G06Q 30/018* (2013.01); *G09B 7/00* (2013.01); *G09B 9/00* (2013.01); *G09B 23/288* (2013.01); *G16H 10/60* (2018.01)

(58) Field of Classification Search
CPC .. G06F 19/322; G06Q 30/018; G09B 23/288; G09B 5/00; G09B 7/00; G09B 9/00; G09B 7/02
(Continued)

(56) References Cited

U.S. PATENT DOCUMENTS 4,583,524 A * 4/1986 Hutchins ................ A61H 31/00
128/898
8,834,175 B1 * 9/2014 Daddi ...................... G09B 7/02
434/322
(Continued)

FOREIGN PATENT DOCUMENTS

JP    1999 H11-249543    3/2001
JP    2005-018365 A      1/2005
(Continued)

OTHER PUBLICATIONS

Wie Chen, et al., "Rythm of Life Aid (ROLA): An Integrated Sensor System for Supporting Medical Staff During Cardiopumonary Resuscitation (CPR) of Newborn Infants," IEEE Transactions on Information Technology in Biomedicine, IEEE Service Center, Los Alamitos, CA, US, vol. 14, No. 6, Nov. 1, 2010, pp. 1468-1474.
(Continued)

*Primary Examiner* — Eddy Saint-Vil
(74) *Attorney, Agent, or Firm* — 24IP Law Group USA, PLLC; Timothy DeWitt

(57) ABSTRACT

A medical training system is disclosed comprising a medical simulation management module, a student record database having a plurality of records relating to training of students, wherein the student record database is connectable to the medical simulation management module, at least one medical training module executable on a training device and comprising scenarios for the training of the students; and a data entry device for entry of student training data to the student record database, the student training data being
(Continued)

indicative of performance of the students on using the at least one medical training module.

6 Claims, 2 Drawing Sheets

(51) Int. Cl.
*G06Q 30/00* (2012.01)
*G06F 19/00* (2018.01)
*G09B 7/00* (2006.01)
*G09B 23/28* (2006.01)
*G16H 10/60* (2018.01)

(58) Field of Classification Search
USPC .................................. 434/265, 267, 262, 322
See application file for complete search history.

(56) References Cited

U.S. PATENT DOCUMENTS

| | | | | |
|---|---|---|---|---|
| 2003/0149759 A1* | 8/2003 | Hetherington | ......... | G06Q 10/06 709/223 |
| 2005/0095572 A1* | 5/2005 | Comer | ..................... | G09B 7/02 434/362 |
| 2005/0251214 A1* | 11/2005 | Parascandola | ....... | G09B 23/288 607/5 |
| 2008/0085501 A1* | 4/2008 | Novack | .................... | G09B 7/02 434/322 |
| 2008/0171311 A1 | 7/2008 | Centen et al. | | |
| 2008/0227073 A1* | 9/2008 | Bardsley | ................ | G09B 23/30 434/267 |
| 2008/0312565 A1 | 12/2008 | Celik-Bitler et al. | | |
| 2009/0035740 A1* | 2/2009 | Reed | .................... | G09B 23/288 434/265 |
| 2009/0148821 A1 | 6/2009 | Carkner et al. | | |
| 2009/0270931 A1* | 10/2009 | Liden | ................... | A61H 31/005 607/5 |
| 2010/0075283 A1* | 3/2010 | Rees | ...................... | G09B 19/00 434/219 |
| 2011/0070572 A1* | 3/2011 | Miller | ...................... | G09B 7/02 434/322 |
| 2011/0117529 A1 | 5/2011 | Barash et al. | | |
| 2012/0123224 A1* | 5/2012 | Packer | ................ | G06F 19/3418 600/301 |
| 2013/0330700 A1* | 12/2013 | Feins | ..................... | G09B 19/00 434/268 |

FOREIGN PATENT DOCUMENTS

| | | | | |
|---|---|---|---|---|
| JP | 2005118187 A | 5/2005 | | |
| JP | 2007-114769 A | 5/2007 | | |
| JP | 2009543611 A | 12/2009 | | |
| JP | 2010-055068 A | 3/2010 | | |
| WO | 2008059394 A1 | 5/2008 | | |
| WO | WO 2008008893 A3 * | 12/2008 | ............. | G09B 23/28 |
| WO | 2009018334 | 2/2009 | | |
| WO | 2011060350 | 5/2011 | | |

OTHER PUBLICATIONS

Jensen, M., et al., "Using e-learning for maintenance of ALS competence," Resuscitation 80, 2009 pp. 903-908, Jun. 5, 2009.
Laerdal Product Information Bulletin 11-002, SimCenter, Apr. 19, 2011.
M. Oermann, "HeartCode BLS with Voice Assisted Manikin for Teaching Students," Teaching With Techonlogy/Basic Life Support, Sep./Oct. 2010, vol. 31 No. 5, pp. 303-308.
Laerdal HeartCode PowerPoint, May 20, 2010.
Laerdal Advanced Video System.
N. Mpotos, B. De Wever, N. Cleymans, J. Raemaekers, M. Valcke and K. Monsieurs, "The power of assessment and feedback successful individualized chest compression training in a self learning station," Universiteit Gent (2012).
N. Mpotos, S. Lemoyne, B. Wyler, E. Deschepper, L. Herregods, P. Calle, M. Valcke and K. Monsieurs, "Training to deeper compression depth reduces shallow compressions after six months in a manikin model," Resuscitation 82 (2011) 1323-1327 (2011).
N. Mpotos, B. De Wever, M. Valcke and K. Monsieurs, "Assessing basic life support skills without an instructor: Is it possible?" BMC Medical Education 2012 12: 58.
N. Mpotos, B. De Wever, N. Cleymans, J. Raemaekers, M, Valcke and K. Monsieurs, "The power of assessment and feedback successful individualized chest compression training in a self learning station," Acta Clinica Belgica, 2012; 67-2.

* cited by examiner

SYSTEM AND METHOD FOR MAINTENANCE OF COMPETENCE

CROSS-REFERENCE TO RELATED APPLICATIONS

This application claims benefit of and priority to U.S. Provisional Patent Application No. 61/600,101 entitled "System and Method for Maintenance of Competence" filed on Feb. 17, 2012.

FIELD OF THE INVENTION

The field of the invention relates to a medical training system, a method for training students in medical matters and a computer program product stored in a non-volatile memory and which when executed on a general-purpose computer enables the general-purpose computer to perform the method.

BACKGROUND OF THE INVENTION

Medical training systems are known in the prior art. One example of a medical training system is a medical simulation system, such as those produced by the Laerdal Medical AS based in Stavanger, Norway. Such medical simulation systems enable the training of students in responding to the medical needs of patients by simulating a medical emergency or other medical procedure. These needs include, but are not limited to, casualty assessment, emergency response, birthing, and cardiopulmonary resuscitation (CPR). Cardiopulmonary resuscitation is an emergency procedure that is performed in an effort to manually preserve intact brain function, until further measures can be taken to restore normal blood circulation and breathing to a patient.

The medical simulation systems often use manikins. The manikin is a life-sized anatomical human model used as a teaching aid in medical education for training students, for example doctors, nurses, paramedics, as well as other learners in, for example, emergency care and resuscitation of humans. A number of companies produce manikins. For example, Laerdal, have produced manikins in various forms since the 1960s. Generally, manikins are three-dimensional models of all or part of a human being and are intended to be as realistic as possible in order to provide the learners with a realistic situation. The manikin can be used to instruct learners using a so-called "training scenario". The training scenarios are designed to be realistic simulations of medical emergencies that might occur in real-life. An instructor can institute one or more of the training scenarios and view how the learner responds to the implemented training scenario.

More recently e-learning systems have been introduced. For example, the Laerdal company has developed a self-directed, computer-based course for obtaining basic life support certification and is marketed under the trade name HeartCode™. The HeartCode system enables students to obtain certification and includes a local database recording the names of the students who achieve certification.

One of the issues involved with medical training is that students need to refresh their knowledge (also termed competence) of the medical simulation. Studies have shown that merely using e-learning techniques for the maintenance of competence in medical skills has been demonstrated to be not sufficiently adequate (see Jensen et al "Using e-learning for maintenance of ALS competence, Resuscitation 80 (2009) 903-908). The Jensen et al. article concluded that the use of an e-learning program in order to maintain or boost competence in a medical school was inadequate. The primary factor influencing these results was the lack of social interaction with the patient.

A number of e-learning systems for medical simulation are known. For example, Laerdal Medical offers a SimStore centre together with the US Company HealthStream, Nashville, Tenn., which is an e-warehouse that supports the distribution and sale of medical simulation content. Further details of the SimStore and related SimCenter product are included in the Laerdal product information bulletin 11-002, dated 18 Apr. 2011. This product information bulletin describes the global launch of the SimCenter product. The medical simulation content in the SimStore is designed to be used with training products and other medical simulation products, such as those produced by the Laerdal Company.

The term student as used in this disclosure is not intended to exclusively mean an undergraduate or college student who is attending an MD course, a B. Med. course or similar. The term "student" is also intended to apply to health-care professionals, such as an already-qualified nurse, doctor or paramedic who requires basic and refresher training to maintain his or her competence. It will be appreciated that the term "student" is therefore widely understood in the context of this disclosure to mean those people undergo training using medical simulation devices, e-learning or practical experience.

One of the issues involved in maintenance of competence in medical procedure with a skilled person, such as a doctor, experienced nurse or paramedic is the need to convince an experienced student of the value of further or refresher training Many such experienced students tend not to take medical training on medical simulation devices seriously because they are involved in day-to-day instances in which this medical training is put to practical use. As a result, such students tend not to perform as well as expected on such devices.

A similar problem is encountered with students who rarely, if ever, are faced with a real-life medical emergency. Such "inexperienced" students also tend not to take the training on the medical simulation system as seriously as they should, because they do not expect to need this training Such "inexperienced" students, as well as other medical personal, tend also to regard such training on the medical simulation systems as being of a lower priority than many of their other tasks. The students therefore avoid going to a specialised training unit, possibly based in another building or at another location, in order to revive their competences and obtain the necessary recertifications. For hospitals and other medical services, the lack of certified personal can be an issue in a medical emergency, particularly if there a later enquiry about the competences of the personnel involved in the medical emergency.

In addition to a traditional medical simulation system, new types of medical training systems and medical monitoring systems have been introduced in order to monitor and evaluate students in real-life situations. For example, US Patent Application Publication No. US 2008/0312565 (assigned to the Board of Regents of the University of Texas system, Austin, Tex. and Laerdal Medical, Stavanger, Norway) describes a CPR sensor including a thin and substantially flat flexible substrate having one or more sensor arrays, a power source, an output interface, a processor or analogue circuit incorporated into a credit-card flat flexible substrate. The CPR sensor of the US '565 publication can be easily carried in a wallet or other personal belonging or item of clothing so that the CPR sensor can be located quickly during an emergency. The CPR sensor is placed on or near to the hands of the person administering CPR and is able to provide immediate feedback to the person administering CPR to indicate that he or she is correctly administering CPR. The incorporation of the output interface enables a transfer of the real-life data to a database for further evaluation at a later stage. The storage of the real-life data in the database can be invaluable when reviewing the person's competence in performing CPR and/or for evaluating the performance of the CPR in the event that there is an enquiry or a lawsuit related to the performance of the CPR.

SUMMARY OF THE INVENTION

This disclosure teaches a medical training system comprising a medical simulation management module and a student record database having a plurality of records that relate to training of students. The student record database is connectable to the medical simulation module. At least one medical training module is executable on a training device and comprises at least one or more scenarios for training of the students. A data entry device is also incorporated which allows the entry of student data to the student record database. The student data is indicative of performance of the students when using the at least one medical training module. The medical training system also includes a certification database which issues (including printing) certifications and further monitors the expiry of such certifications.

The medical training system of this disclosure enables the recording of medical training data and storage in a central database. The medical training data is not merely indicative of training on a medical simulation system, but also is relevant to data gathered during a real-life performance of a medical procedure on a patient. The medical training system of this disclosure therefore provides a one-stop shop in which all relevant medical training data including medical data gathered during monitoring of the real-life performance is collected in a single database and the student record database can be used to evaluate those areas of medical practice in which the student may be weak. It will be appreciated that the student record database includes not only data from training scenarios performed on a manikin or other training devices, but also records relating to the performance of the student during a real-life emergency. Such collection of records means that a student's performance in real-life can also be reviewed and any necessary training be organised fairly quickly. If the student is found to be performing a medical procedure correctly in real-life, there is no need for him or her to have medical training involving the use of simulators. This will save valuable student time, and make the use of the medical simulators more efficient.

In addition, the student record database enables the recertification of students to be performed in a timely manner. The medical training system can review the expiry dates of the existing certification and review those areas in which the student is under-performing (or has not recently performed) and automatically set up an appointment for the student to undergo a scenario for additional training and therefore the maintenance of competence.

In one aspect of the invention, the training device could be a personal computer, a smartphone or tablet device in order to perform part or all of some of the medical training. It was noted above, however, that Jensen and his colleagues (see Jensen et al 2009) had indicated that the use of e-learning is not adequate and that therefore the training device should be additionally a manikin or similar.

In a further aspect of the invention, the medical training system can also incorporate or have access to a certification database holding the certifications of the students. This certification database can be connected to a national or international certification database, as appropriate.

In one aspect of the invention, the medical training system is further provided with a data entry device, which can be operated, by an instructor or an invigilator. The data entry device is able to record medical procedures being carried out by the student in the certain circumstances.

In one further aspect of the invention, the data entry device further comprises a monitoring card that is able to monitor the performance of the student on a real-life patient during a real-life emergency. The data entry device stores records relating to the performance of the student during the real-life emergency and, when connected later to the medical training system is able to transfer this data through to the student record database for analysis by the medical training system.

The disclosure also teaches a method for training a student in a medical procedure and comprises determining student requirements, for example by analysis of a student record database, and enabling at least one of a medical training module on a training device or a recording of a real-life situation. The results of the medical training module or the recording of the real-live situation can be evaluated so see whether the results meet specified requirements. Such specified requirements include those set by law or by individual standard and/or certification bodies. If such results do meet the specified requirements then a certification for the student can be issued. Alternatively, the student may be required to undergo further training.

DETAILED DESCRIPTION OF THE INVENTION

The invention will now be described based on the drawings. It will be understood that the embodiments and aspects of the invention described herein are only examples and do not limit the protective scope of the claims in any way. The invention is defined by the claims and their equivalents. It will be understood that features of one aspect or embodiment of the invention can be combined with a feature of a different aspect or aspects and/or embodiments of the invention.

Figure 1:
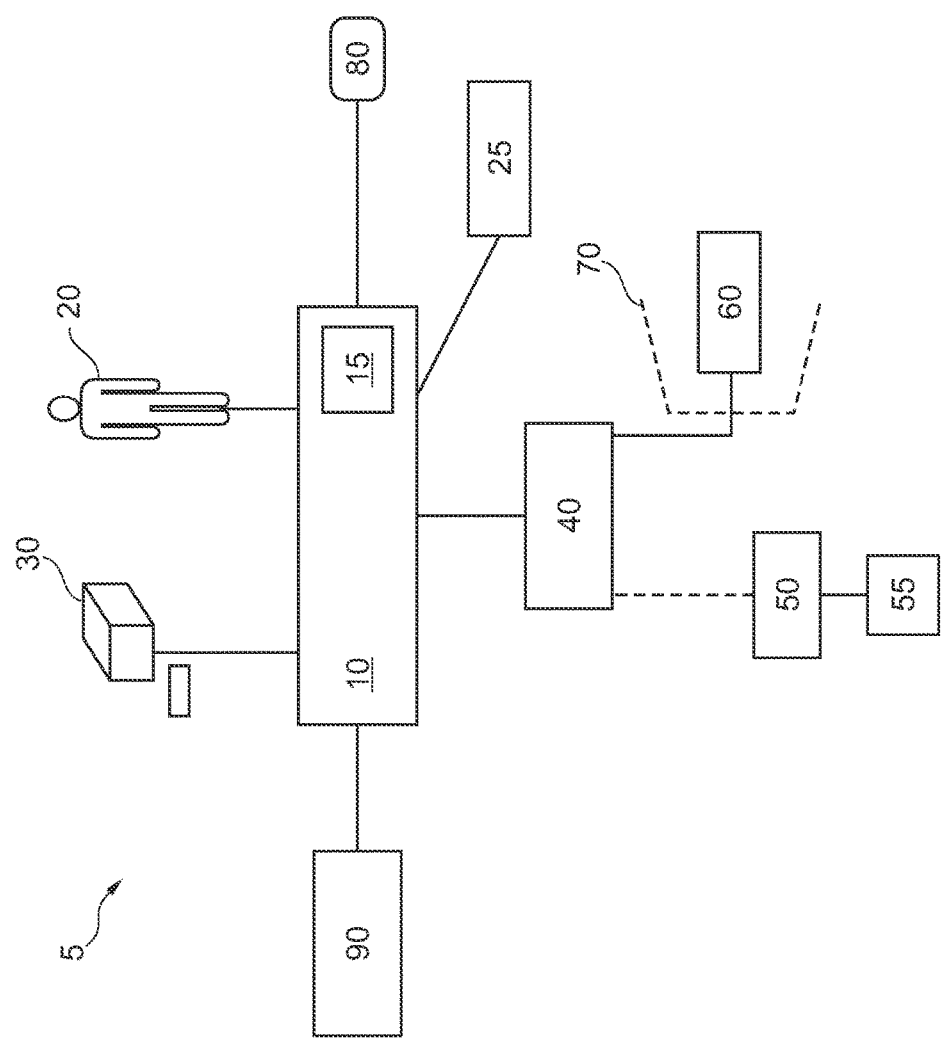
FIG. 1 shows an overview of the medical training system.

A medical training system 5 is shown in an architecture view in FIG. 1. The medical training system 5 has a central administrative module 10 that is running on a general-purpose computer, such as a server. It will be appreciated that the central administrative module 10 may be run as a local sever or a remote server or be part of a module running on a cloud server. The central administrative module 10 includes one or more medical training modules 15. The medical training modules 15 include, but are not limited to training scenarios with simulations of medical procedures such as cardio pulmonary resuscitation (CPR) or other advanced life support cases. It will be appreciated that many such training modules 15 are possible and that variations of the training modules 15 are possible. For example, one of the medical training modules 15 may include training scenarios relevant to an adult but a similar medical procedure formed on an infant requires a different or adapted medical training module 15 because of a different training scenario.

A manikin device 20 is also connected to the central administrative module 10. The connection between the manikin 20 and the central administrative module 10 can be by cable and/or wireless, but is not limiting of the invention.

A personal computer or other form of display terminal 30 is connected to the central administrative module 10 by cable and/or wireless. A student and/or an instructor can operate the personal computer 30. The personal computer 30 enables access to the training modules 15 running on the central administrative module 10 and will enable access to patient records 60, if the student or instructor has sufficient access rights to enable access to this private data. It will, however, be appreciated that laws governing access to such data are extremely restrictive and thus the training modules 15 may write data to such patient records 60, but rarely allow access. It may be possible to allow access anonymously.

A data manager 40 is connected to central administrative module 10 by cable or wireless. The function of the data manager 40 is to extract from the central administrative module 10 any relevant data relating to performance of the student when using the medical training modules 15. The data manager 40 can collect data from the manikin 20 and/or from the personal computer 30. The data manager 40 can pass the data to the patient records database 60 (as disclosed above) and/or write data into the student records database 50 includes the names of the student, generally as entered through the personal computer 30, and also any data relating to the types of medical competence for which the student is trained as well as expiry dates of certification requirements for a particular medical competence. The student records database 50 also includes verifiable keys that can be accessed by, for example, an employer to verify any information and certify that the information is genuine.

One illustrative example of such a certification is the requirement in the United States to be regularly certified for CPR. The certification for CPR can be obtained by running an appropriate one of the training modules 15 on the manikin 20. The results of the performance of the student on the manikin 20 are recorded by the central illustrative module and passed through the data manager 40 to the student records database 50. The student records database 50 can then print an appropriate certification and/or by a printer 55 pass an electronic form of the certification to another certification database. The other certification database could be a centralised database recording nationwide the certifications.

The student records database 50 maintains a list of expiry dates of the certifications of the medical competences for the students recorded in the student records database 50 and/or on the central administrative module 10. The student records database 50 is therefore able to inform the student that the certification is about to expire and to notify the student that such certification can be performed. The student records database 50 can also inform the student's employer of the expiry of the certification, if appropriate to enable the employer to take appropriate action if the student is no longer adequately certified. The notification will take the form of an email generated by the certification database 50 and then sent through an email system using an appropriate interface, such as a MAPI (messaging application programming interface) using a remote procedure call (RPC).

It will be noted that there is currently no US nationwide or other central certification database provided. This may or may not be introduced in future, as there are issues regarding confidentiality.

The patient records database 60 is one of the most sensitive databases and is generally protected by an additional isolation 70, such as a firewall, to prevent unauthorised access. The patient records database 60 is generally accessed only when a medical procedure is performed on a real-life patient as opposed to a performance of the training scenario on the manikin 20 and the data relating to the performance of the student on the real-life patient is incorporated into the central administrative module 10.

The introduction of a CPR sensor, such as disclosed in US Patent Application Publication No. US 2008/0312565, enables data from the real-life patient to be passed to the central administrative module 10 and incorporated into the certification database 50. For example, an experienced student does not need to train on the manikin 20 if the experienced student has performed sufficiently well on the real-life patient, as evidenced by the data on the CPR card 80. For this purpose, the CPR card 80 incorporates a card memory for storage of data a data output device that enables wireless transfer of the data stored on the card memory in the CPR card to the central administrative module.

The card memory is in the form of an EEPROM connected to a serial single-ended bus. The bus uses the I$^2$C protocol (or similar) for transferring the data internally within the bus. The wireless transfer of the data is carried out using the ISO/IEC 15693 standard. The card memory stores data which includes, but is not limed to, card life time use statistics including an overview of all of the so-called "resuscitation episodes" that which the card has been registered, together with a count of the number of times for which the card has been used and the total amount of time during which the card has been used.

Each use of the card in a training session and/or a real-life emergency session is designated as a "resuscitation episode". The card memory further includes individual episode statistics. In a current implementation of the card, data relating to the sixteen most recent resuscitation episodes is stored. It will be appreciated that the limit on storage is arbitrary and depends on the amount of storage available. Statistics relating to the individual resuscitation episodes include, but are not limited, compression depth, rate, compression in activity, how many of the compressions lie within guidelines set by the American Heart Association (or similar) as well as histogram data showing distribution of depth, rates and inactivity for a number of the individual episodes.

It will be noted that the CPR card include an accelerometer and a timing device in order to ensure that the CPR procedure is correctly carried out and to establish the data relating to the compression depth and rate. Data from the accelerometer and the timing device are stored in the card memory. The skilled person will realize that the CPR card 80 is only one example of a data entry device that can monitor the performance of the student on the real-life patient. The teachings of the CPR sensor are disclosed in US Patent Application Publication No. US 2008/0312565 and are incorporated herein by reference.

A quality control system 90 is connected to the central administrative module 10 for monitoring the quality of the training. The quality control 90 will generally have access to anonymous data from the central administrative module 10, i.e. without access to the student's names or other identification and/or the patient's names and/or other identifications.

It will be appreciated that the manikin 20 shown here does not need to be placed in a central training unit. On the contrary, in order to ensure that students are regularly trained the manikin 20 will often be housed in a side room near a ward of a hospital. This will allow the student to undertake regular medical training whenever it becomes convenient for him or her. There is no need for the student to register for a training course in order to obtain recertification.

The advantage of having the manikin 20 near the student's work place is also that the student can be instructed, for example by email, to undertake regular refresh courses in order to maintain his/her competence. The refresher courses are one example of the medical training modules 15 and different refresher courses can be given at different intervals.

The personal computer 30 will also enable the student to undertake regular and continuous education on various aspects of medical procedure. For example, the guidelines of the American Heart Association on CPR have recently been updated. The central administrative module 10 can inform the student about the update and arrange for the student to arrange an appropriate one of the medical training modules 50 in order to be updated on the revised medical procedure. The central administrative module 10 can record the student's completion of the training and provide feedback to the student and/or the quality control 90 to enable important action to be taken.

Figure 2:
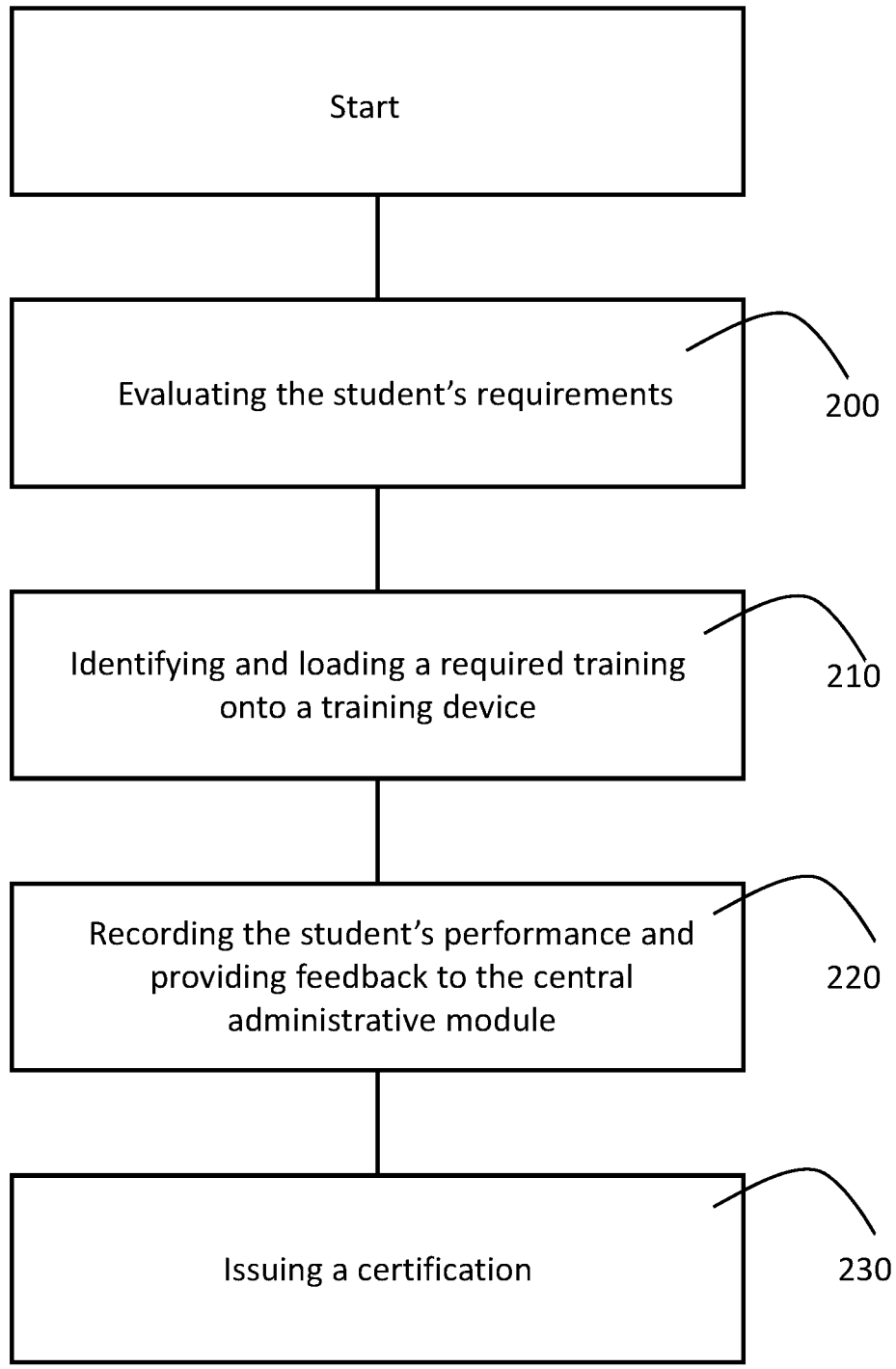
FIG. 2 shows a flow diagram of the method for training students in medical matters.

FIG. 2 shows a workflow according to one aspect of this disclosure in which a student is required to undertake initial or updated training in a medical procedure. In a first step 200, the student's requirements are evaluated. The evaluation depends very much on the educational level of the student and/or the current requirements of the student and/or the hospital (or other medical location, such as a doctor's surgery or emergency care vehicle). Once the student requirements have been evaluated, In step 210, an appropriate one of the training modules 15 for a required training scenario is identified and loaded onto a training device. The training device could be, in this aspect of the invention, the manikin 20 and/or the personal computer 30. It was noted above that some of the medical training modules 15 are appropriate only for use on the personal computer 30 whilst others have functions that can only be performed on the manikin 20.

In step 220 manikin 20 and/or the personal computer 30 record the student's performance when performing the medical training module 15 and provide feedback to the central administrative module 10. In particular this feedback can include whether the student requires further training and/or has meet the requirements to obtain certification which can be issued in step 230. In one further aspect of the invention, an instructor or an invalidator has a data entry device 25 that he or she uses to record the student's performance and to pass details of the performance to the central administrative module for review and recording.

It will be appreciated that the functions of the central administrative module 10, the quality control 30 and the data manger 40 overlap to a certain extent. These are generally implemented as computer programs running on a general-purpose computer and the instructions are stored on a non-volatile memory device. It will be further appreciated that the components may be implemented in different manner, depending on the general-purpose computer system on which they are running.

In one further aspect of the invention the data entry device 25 may be a code sheet completed by a nurse and logged in an appropriate log. Any data from the log or code sheet can be transferred either electronically or by manual entry to the central administrative module 10.

One example of the data entry device 15 used in this disclosure is the advanced video system developed by Laerdal and described in a press release, dated 30 Mar. 2011.

The invention claimed is:

1. A medical training system comprising:
    a central administrative module including at least one medical training module, wherein said central administrative module is running on a computer;
    a student record database having a plurality of records relating to training of students, wherein the student record database is accessible by the central administrative module;
    a data entry device for entry of student training data to the student record database, said data entry device comprising a monitoring sensor configured to monitor performance of students on a training device and a patient in real-life at a medical location, wherein said training device is a manikin and wherein the student training data is indicative of performance of the students of a medical procedure on the training device and the patient in real-life, wherein the student training data of the performance of the students of the medical procedure on the training device and the patient in real-life is collected in the student record database for evaluating the performance of the students of the medical procedure on the training device and the patient in real-life, wherein the evaluation comprises comparison of the student training data indicative of performance of the students of the medical procedure on the training device and the patient in real-life with specific requirements depending on an education level of the student, current requirements of the student, and current requirements of the medical location and wherein the training device provides feedback to the central administrative module on whether the students require further training;
    wherein the at least one medical training module is executable on the training device and comprises scenarios for the training of the students, wherein only a required one of the at least one medical training module is identified and loaded onto the training device depending on the evaluated performance of the students of the medical procedure on the training device and the patient in real-life; and
    a certification database configured to issue and monitor certifications of the students, wherein a certification is issued on completion of only the required at least one medical training module.

2. The medical training system of claim 1, wherein the data entry device is operable by one of an invigilator or an instructor.

3. The medical training system of claim 1, further comprising a patient record database connectable to the medical simulation management module.

4. A computer-implemented method for training a student in a medical procedure comprising:
    determining student requirements;
    loading an appropriate one of at least one medical training module onto a training device, wherein said training device is a manikin;
    recording a real-life situation by placing a recording device proximate to the training device and a patient in real-life at a medical location; and recording a performance of the student in performing the medical procedure on the training device and the patient in real-life to provide feedback to a central administrative module whether the student requires further training, wherein said central administrative module is running on a computer;

recording student training data, wherein the student training data is indicative of performance of the student of the medical procedure on the training device and the patient in real-life;

collecting the student training data in a student record database;

evaluating by the central administrative module whether the performance of the student of the medical procedure on the training device and the patient in real-life meet specified requirements, wherein said specific requirements depend on an education level of the student, current requirements of the student, and current requirements of the medical location;

identifying and loading only a required one of at least one medical training module executable on the training device depending on the evaluated performance of the student of the medical procedure on the training device and the patient in real-life; and issuing a certification on completion of only the required one of the at least one medical training module.

5. The method of claim 4, further comprising transfer of the recording to a student record database.

6. The method of claim 4, wherein the issuing of the certification comprises passing an electronic record of the certification to another database.

* * * * *